(12) United States Patent
Akkerman et al.

(10) Patent No.: US 8,067,722 B2
(45) Date of Patent: Nov. 29, 2011

(54) METHOD AND SYSTEM FOR INSPECTING BOTTLES

(75) Inventors: Jensen Peter Akkerman, Huizen (NL); Bernardus Cornelis Johannes Landman, Boskoop (NL)

(73) Assignee: Heineken Technical Services B.V., Zoeterwoude (NL)

( * ) Notice: Subject to any disclaimer, the term of this patent is extended or adjusted under 35 U.S.C. 154(b) by 0 days.

(21) Appl. No.: 10/542,971

(22) PCT Filed: Feb. 27, 2004

(86) PCT No.: PCT/NL2004/000150
§ 371 (c)(1),
(2), (4) Date: Apr. 19, 2006

(87) PCT Pub. No.: WO2004/088295
PCT Pub. Date: Oct. 14, 2004

(65) Prior Publication Data
US 2006/0208172 A1    Sep. 21, 2006

(30) Foreign Application Priority Data

Feb. 28, 2003 (NL) ........................... 1022810

(51) Int. Cl.
*G01N 21/90* (2006.01)
*G06K 9/00* (2006.01)
(52) U.S. Cl. .................... 250/223 B; 382/142
(58) Field of Classification Search .......... 250/223 B, 250/573, 574, 221, 222.1, 559.4, 559.44, 250/223 R, 222.2, 208.1; 356/239.5, 239.6, 356/426, 427, 239.4, 239.1, 239.7, 239.8, 356/240.1, 436, 439, 441, 442; 382/142, 382/141, 143, 149, 151, 152, 153; 209/524, 209/585, 701, 526
See application file for complete search history.

(56) References Cited

U.S. PATENT DOCUMENTS

| | | | |
|---|---|---|---|
| 3,496,369 A | | 2/1970 | Makino et al. |
| 3,528,544 A | | 9/1970 | Noguchi et al. |
| RE28,984 E | * | 9/1976 | Drinkuth et al. ............. 348/127 |
| 4,605,851 A | * | 8/1986 | Ometz et al. ............. 250/223 B |
| 4,608,709 A | * | 8/1986 | Hedler et al. ............... 382/142 |
| 5,072,108 A | * | 12/1991 | Ishikawa ................. 250/223 B |
| 5,305,391 A | * | 4/1994 | Gomibuchi ................. 382/142 |
| 5,523,560 A | * | 6/1996 | Manique et al. .......... 250/223 B |
| 6,275,603 B1 | * | 8/2001 | Cronshaw et al. ........... 382/142 |
| 6,882,422 B2 | * | 4/2005 | Katane et al. ................ 356/427 |
| 2003/0063281 A1 | * | 4/2003 | Katane et al. ................ 356/427 |

FOREIGN PATENT DOCUMENTS

| | | |
|---|---|---|
| EP | 0 303 175 | 2/1989 |
| EP | 0 418 005 A1 | 3/1991 |
| GB | 798144 | 7/1958 |
| WO | 97/14956 | 4/1997 |
| WO | 00/77499 A1 | 12/2000 |

* cited by examiner

Primary Examiner — Thanh X Luu
Assistant Examiner — Jennifer Bennett
(74) Attorney, Agent, or Firm — Merchant & Gould P.C.

(57) ABSTRACT

The present invention relates to a method for inspecting packagings for a liquid product, such as drinks, including: setting a packaging into rotation, irradiating the packaging during the rotation with a radiation of a predetermined wavelength, making at least one series of at least two recordings of at least a part of the content of the packaging during the rotation, with an image recording device suitable for making recordings at the predetermined wavelength.

17 Claims, 6 Drawing Sheets

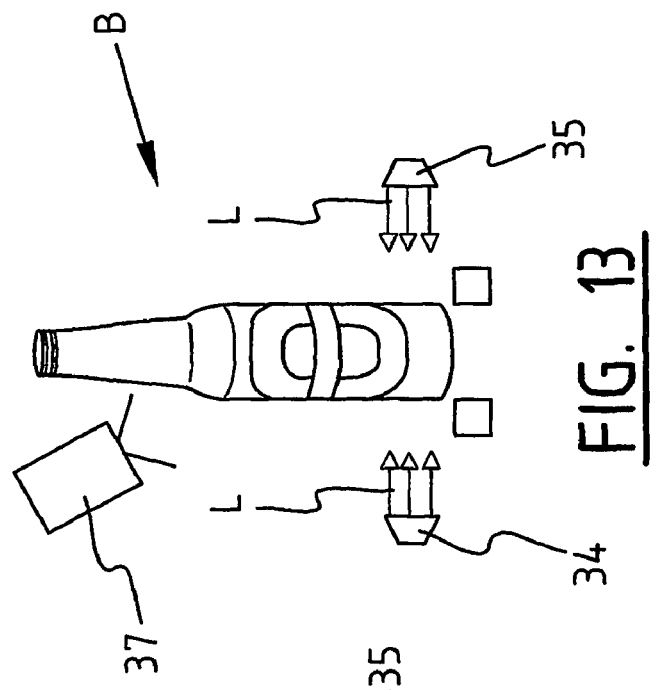
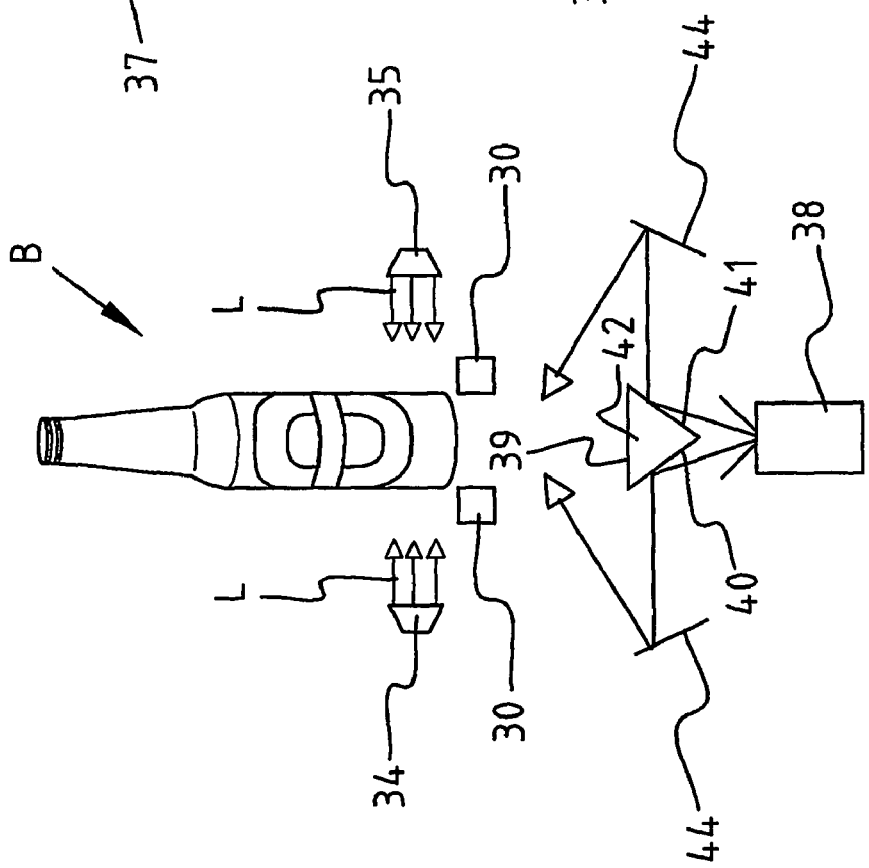
FIG. 13
FIG. 12

METHOD AND SYSTEM FOR INSPECTING BOTTLES

Methods and systems have recently been developed for inspecting packagings such as drink-containing bottles. The occurrence of for instance glass splinters in beer can result in corporate losses as a result of for instance rejected batches, return operations and damage to the company reputation because the presence of glass splinters will be the subject of negative press reports.

From the international patent application PCT/NL96/00049, which is deemed as interpolated herein by means of reference, is known a method and apparatus for detecting extremely small glass splinters in filled beer bottles. Each filled bottle is herein rotated for a short time in a separate station and then brought quickly to a standstill, whereby movements of the small glass splinters can be detected using a light source-camera system and associated image processing.

This method functions well enough in practice but requires a complex apparatus in the filling line of a brewery or soft drink manufacturer. Carrying out an inspection using such a method takes on average about 2.1 seconds per bottle. Such a system is moreover expensive because, in order to achieve the high average speed of for instance 60,000 bottles per hour of a filling line, a plurality of rotation and image recording stations is required, for instance 36.

So as to improve the above stated method, the present invention provides a method for inspecting packagings for a liquid product, such as drinks, comprising steps for:
setting a packaging into rotation,
irradiating the packaging during the rotation with a radiation of a predetermined wavelength,
making at least one series of at least two recordings of at least a part of the content of the packaging during the rotation, this with an image recording device suitable for making recordings at the predetermined wavelength.

A method according to the present invention has the advantage that a good inspection is achieved in a shorter time per packaging, whereby a relatively small number of rotation and image recording stations (detection units, inspection units) is required. When an embodiment according to the present invention is applied, an inspection takes an average of 0.7 second per bottle. One result hereof is that inspection systems can be realized more easily and more cheaply by applying the method.

A system with a smaller number of rotation and image recording stations, for instance 12-24, will suffice to perform an embodiment of a method according to the present invention.

In a further embodiment the packaging is situated in substantially the same rotational position relative to the recording device during successive recordings of the series. Successive images are made of a bottle revolving on its vertical axis. During rotation of the bottle at least 1× an image is recorded of the (continuously revolving) bottle. These images are stored. Each image is compared to a preceding or subsequent image of therefore the same bottle with 360 rotation difference. When these two successive images are compared, the bottle will be situated in the same position while a piece of glass possibly present in the bottle will however have another position in the image. This glass displacement between the two images can be detected, for instance by subtracting the images from each other. If anything remains in the image, then glass is present. Subtracting the images from each other is a per se known principle which is applied inter alia in the inspection of labels. A bottle with a glass particle will be detected.

It is possible to already carry out the inspection during the rotation (when the bottle is revolving and the glass is moving in relation to the bottle). The spin and inspection can in principle be carried out together in about 0.7 second, whereby for instance only 18 (12-24) inspection units are required to realize a capacity of 60,000 bottles per hour.

According to a further embodiment successive recordings of the series are made with an intervening time interval of a predetermined duration. A relatively simple method of activating the camera for the purpose of taking a picture hereby becomes possible.

The rotation speed is preferably varied during the period in which the recordings of a series are made. A difference between the speed of the content of the packaging and the packaging is hereby realized.

There is further a preferred embodiment wherein the rotation direction is varied during the period in which the recordings of a series are made. Changes in speed enhance the effect of the difference in speed.

It is advantageous to make a plurality of recordings from a different angle of view in relation to the packaging. It hereby becomes possible for instance to detect particles in packagings on which labels have already been arranged.

Image information from the images of a series is preferably compared in order to detect the presence of undesired particles, such as glass particles, in the packaging.

A further aspect of the present invention relates to a system for performing a method as claimed in one or more of the foregoing claims.

Further advantages, features and details of the present invention will be elucidated on the basis of the following description of preferred embodiments thereof, with reference to the annexed drawing, in which:

FIGS. 9-13 show a diagrammatic view of further embodiments according to the invention.

Figure 1:
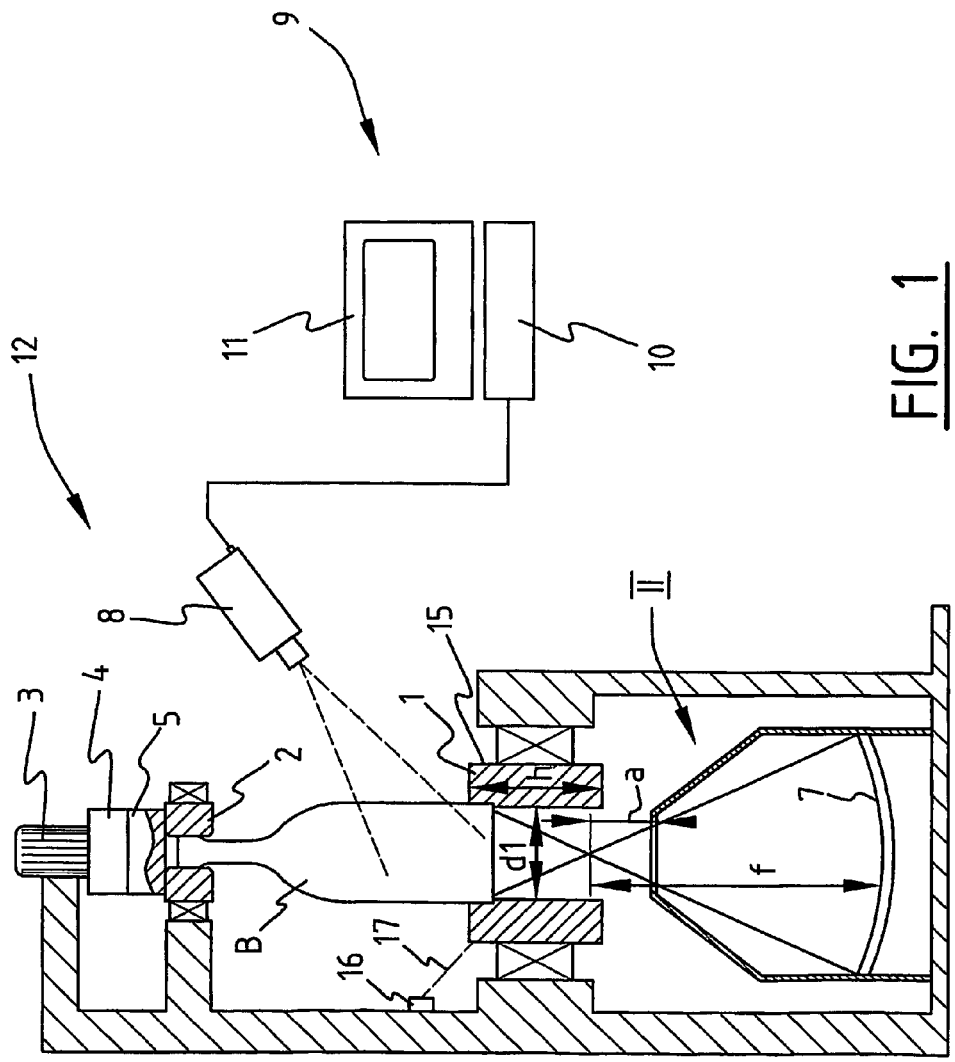
FIG. 1 shows a schematic view of an inspection station according to the present invention.

One beer bottle B at a time (FIG. 1) is clamped in a detection unit 12 between a ring 1 and a head 2. A motor 3, which is coupled to head 2 via a speed-reducing mechanism 4 and an optional brake 5, serves to set the bottle into rotation. Ring 1 and head 2 are therefore mounted rotatably relative to a frame 6. Light from a light source 7 is further cast into the bottle and recordings are made of the content of the bottle. Because there are differences in the rotation speed of the bottle and the liquid in the bottle owing to mass inertia, the content will move relative to the bottle. If recordings are now made at different moments using a CCD camera 8, the content will be situated relative to the bottle at a position other than the bottle in successive recordings. Use is made of this to detect for instance glass particles.

The detection unit further comprises an activation signal generating unit, (e.g. a laser trigger) for creating a signal on the basis of which a camera 8 makes a picture. A laser transmitter/detection unit 16 emits a laser beam 17 in the direction of a reflector 15 on a rotating part of the detection unit. If the reflector passes through the laser beam, this latter is reflected and the reflected beam is received by detection unit 16. A signal is then sent to the camera on which a picture is taken.

An alternative hereto is that the motor generates a position signal to the camera, on the basis of which this latter takes a picture.

The image information is processed in computer 10 and can be displayed on screen 11.

In addition to the above described advantages, embodiments described hereinbelow have the further advantages compared to the prior art that:

- inspection can take place directly during rotation of the bottle,
- the bottle does not have to be physically stopped and held still,
- the bottle can be inspected from a number of sides instead of from one side, thereby increasing the reliability of inspection,
- fouling behind a label, (heavy) scuffing, embossing or pre-printed bottle can be detected,
- the machine can be placed after the labelling device, whereby flexible line lay-outs are possible and the machine can be placed as last in the line, and a real final inspection is therefore possible,
- there is less mechanical complexity, whereby the mechanical reliability and availability of the machine (OPI) improves,
- because the inspection units are individually controlled, an optimal spin profile can be implemented per inspection unit,
- in the case of a line stoppage all bottles present in the carrousel can be inspected, whereby in the case of a line stoppage there are no uninspected bottles (which result in product loss and waste).

Figure 2:
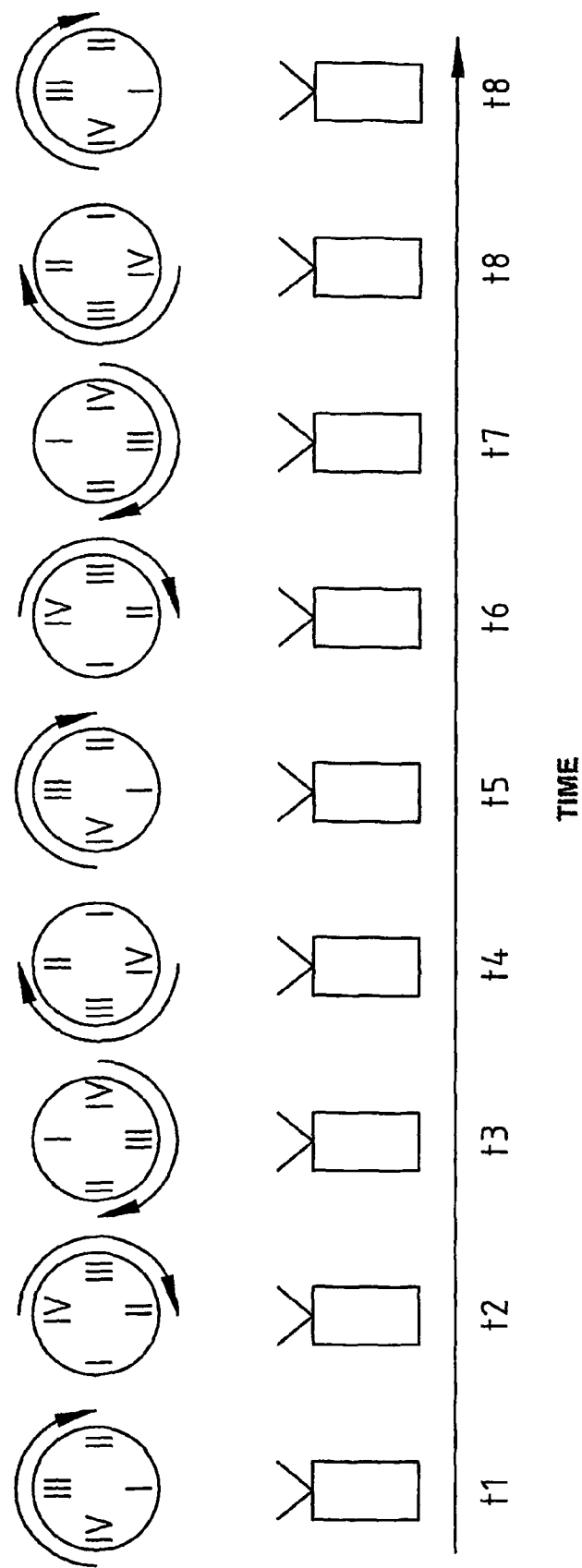
FIG. 2 shows a time diagram of a recording schedule according to an embodiment of the present invention.

In addition to recording a series of images consisting of one picture per rotation, it is also possible to record a plurality of images per rotation (for instance at 0°, 90°, 180° and 270° or more (FIG. 2) with view I, II, III, and IV respectively). Images which are recorded at a determined angle are then compared to a subsequent image recorded 360 after this determined angle. This is shown in the following time diagram (N.B. in top view: the bottle rotates about its vertical axis but is otherwise stationary relative to the camera):

On the basis of this time diagram the following table is compiled for the case that recordings of 4 images per rotation are made, in which is indicated which part of the bottle is being shown at a particular moment in time:

| | | | | |
|---|---|---|---|---|
| image (t1) | I | | | |
| image (t2) | | II | | |
| image (t3) | | | III | |
| image (t4) | | | | IV |
| image (t5) | I | | | |
| image (t6) | | II | | |
| image (t7) | | | III | |
| image (t8) | | | | IV |
| image (t9) | I | | | |
| etc. | | | | |

Herefrom is made the following table which indicates at what times a particular part of the bottle is being shown. If no movement is detected between the two successive images of the same particular part of the bottle, no glass or contamination has been found.

Pictures can be taken at for instance the following points in time:

| | |
|---|---|
| I | t1, t5, t9, t13, etc. |
| II | t2, t6, t10, t14, etc. |
| III | t3, t7, t11, t15, etc. |
| IV | t4, t8, t12, t16, etc. |

Figure 3:
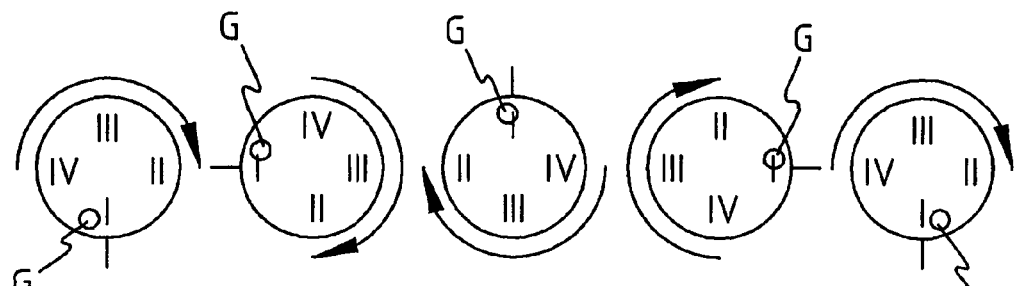
FIG. 3 shows a time diagram according to the embodiment of FIG. 2.

The movement of the glass relative to the bottle is realized as follows (FIG. 3):

When the bottle undergoes an angular displacement, the liquid in the bottle will come into motion more slowly than the bottle. The (glass) particle (G) in the liquid therefore comes into motion more slowly than the bottle. The position of the (glass) particle compared in two images (with substantially 360 difference in bottle rotation relative to each other) will change when the rotation speed of the bottle is increased.

When the rotation speed of the bottle is decreased, the liquid in the bottle will rotate more rapidly after a time than the bottle. The (glass) particle in the liquid will then also rotate more rapidly than the bottle. The position of the (glass) particle compared in two images (with substantially 360 difference in bottle rotation relative to each other) will change when the rotation speed of the bottle is decreased in similar manner as stated when the rotation speed is increased.

As addition to the above method of generating relative movement, use can also be made of the period immediately after start-up of the bottle rotation. At that moment the (glass) particle will, owing to the inertia of movement, still be at rest while the bottle is already moving. At this stage, which preferably lasts about 0-0.3 sec., with a correct choice of exposure and camera shutter time the bottle will be shown out of focus and the (glass) particle will be shown sharply in focus or moving very slowly. The (glass) particle can be detected by applying per se known image processing techniques.

It will be apparent that it is also possible with this method to inspect a larger or smaller number of parts of the bottle. The advantage compared to other methods, including the patent (WO 97/14956) is that the bottle is inspected from a plurality of sides, whereby the chance of detection is increased (or the inspection time can be shortened while the chance of detection remains the same). This advantage is of particular importance in the case of pre-labelled bottles and scuffed bottles.

In order to enable recording of the above series of images the use of asynchronous reset cameras is to be recommended. These are cameras activated (triggered) by an external signal to start the recording of an image. In this application this can take place by using a position feedback signal coming from a detection unit.

Figure 4:
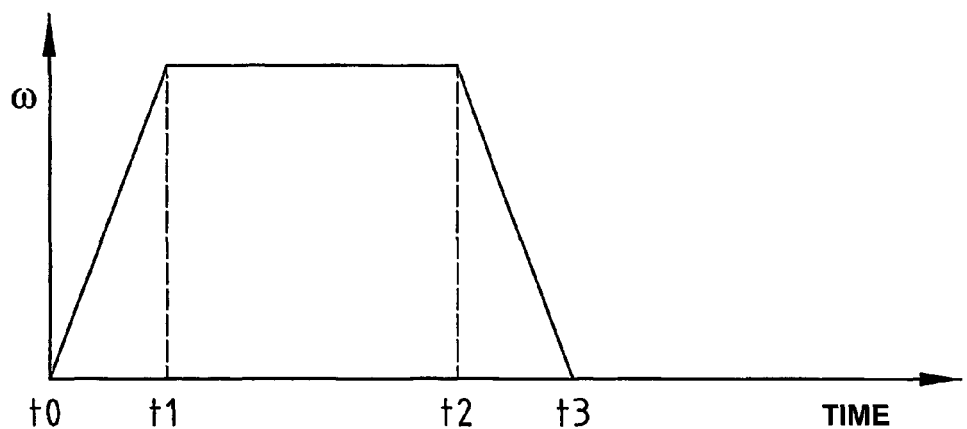
FIGS. 4-8 show a time diagram of different embodiments according to the present invention.

The rotation pattern can be adjusted with this method such that an optimal movement is achieved during recording of images, and thereby detection of possible particles (FIG. 4). The concept of rotation profile is important for this purpose. The rotation profile shows the angular speed of the bottle on its vertical axis as a function of time. A simple example is:

t0-t1: start-up
t1-t2: continuous rotation
t2-t3: braking

It is possible with the method to record and process images during the whole period t0 to t3.

Figure 5:
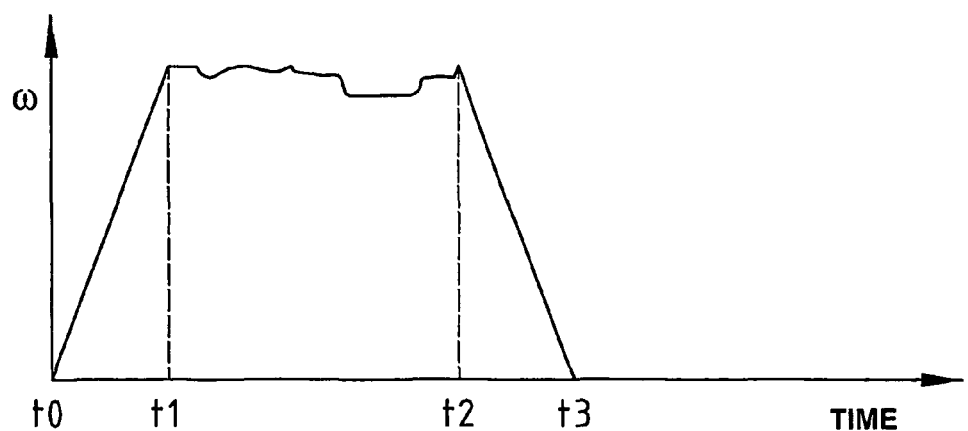

It is particularly advantageous to continue varying the angular speed (FIG. 5) because the particle then remains moving continuously in relation to the bottle.

Figure 6:
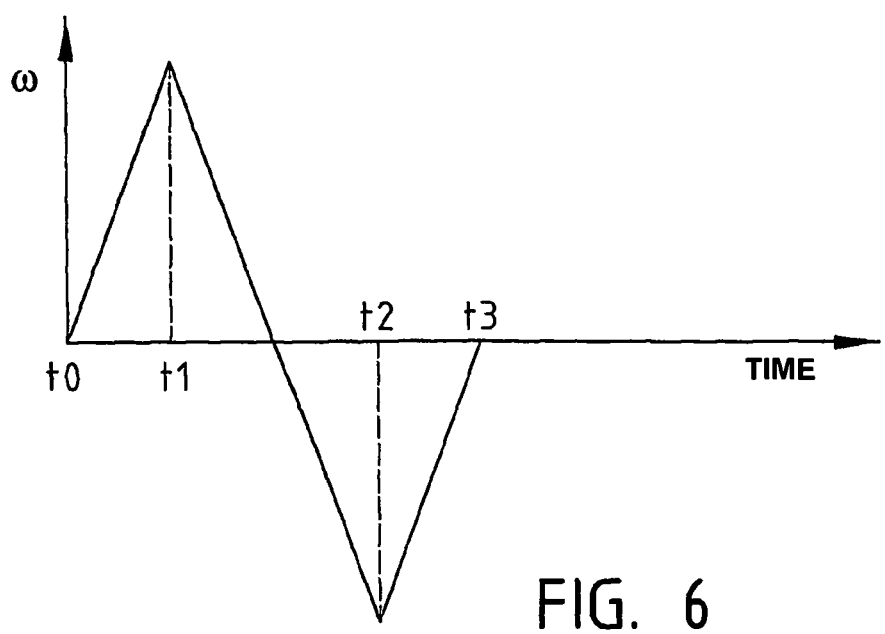
Figure 7:
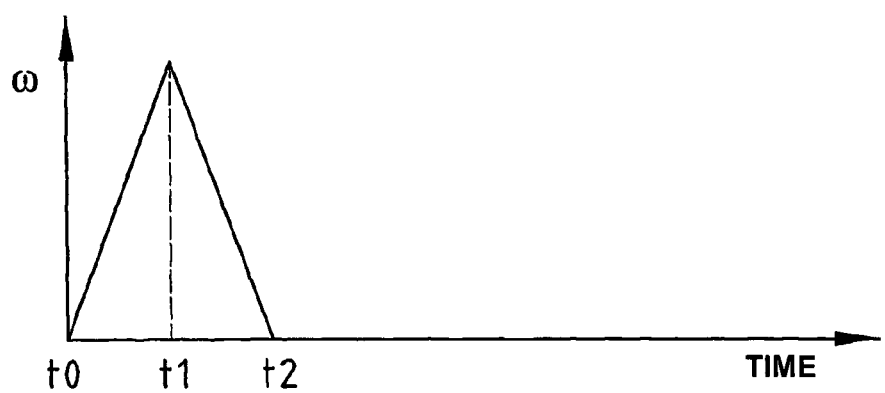
Figure 8:
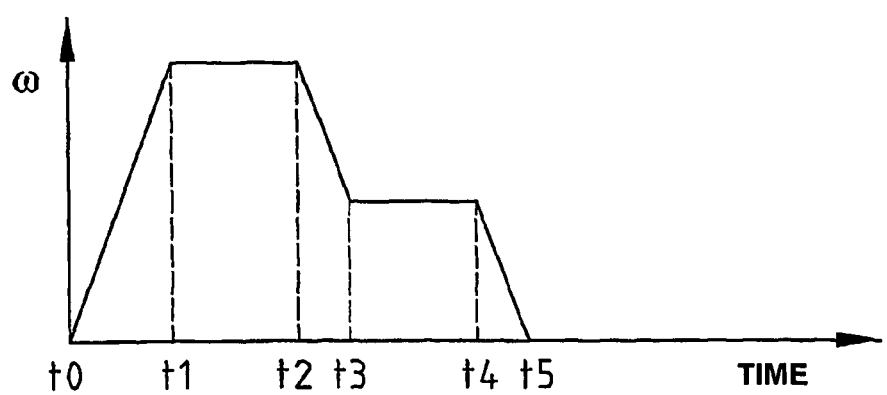

Also possible are more complex (for instance reverse rotation) or very short rotation profiles (FIG. 6, 7). Very short inspection times can hereby be realized, which can result in a very compact machine. An optimal rotation profile (FIG. 8) can also be set for specific products, for instance syrup.

Integration with other, already existing inspections which are carried out in practice on a bottle is made possible by this method of camera per detection unit with separately controlled motor:

360 Label inspection making use of bottle rotation,

Side wall inspection of decorated and embossed bottles, and for instance

Foil detection.

A number of cameras in the fixed world can further be used for further inspections wherein the bottles are oriented.

Data communication can be minimized by linking motor control and image recording triggering by means of intelligent control.

Image series allocation to different PCs can be realized by means of for instance the Firewire protocol (IEEE 1394 standard) or by fast PCs or by multiplexer technology.

The relative movement of the (glass) particle to be detected in the two images, with 360 difference, in relation to the rotating bottle must be great such that software detection through movement detection is possible (because position of glass particle changes).

In a further embodiment the image recording is carried out at a regular time interval and at unknown angular displacement (synchronous reset camera) instead of at an unknown moment and regular angular displacement of the bottle (asynchronous reset camera); The advantage hereof is a simple camera activation. It is more complicated here that the recorded images of a series can be/are of different sides of the bottle, whereby owing to the visible differences between the sides subtraction images will not be black even if (glass) particles are not present. With a good dark field illumination the orientation of the bottle is not important because the side, and therefore also the differences between the sides, will then not be visible in the image (black image−black image=black image). If the dark field illumination is not perfect, it is possible by means of image processing techniques to distinguish reflections from (glass) particles.

Further embodiments according to the present invention comprise:

a carrousel with between 12-24 detection units.

Such a carrousel can be placed in per se known manner in a filling line for bottles. A further variant is a detection line with for instance fixed cameras, wherein the bottles advance one after another during the detection in per se known manner;

bottle orientation feedback means per detection unit (for controlling the moment of camera triggering);

a drive unit per detection unit (e.g. stepping or servo motor with position feedback). One drive can optionally be used for all detection units;

a camera per detection unit;

image field for the images for recording not only on the underside of bottle but now also on the whole bottle for the purpose of inspecting foils and detecting floating objects;

(Firewire) IR camera 80 frames/sec or more;

Infrared illuminator with (modified) dark field illumination;

colour cameras for inspecting labels, caps, and/or filling level of bottles;

image processing computers (IPPs) and communication computers (COMMPC);

optical slip ring for video and other data transfer;

hardware for industrial environment: camera, illuminator, system housing, IPP PC, COMMPC. This means being in accordance with for instance IP65.

Figure 9:
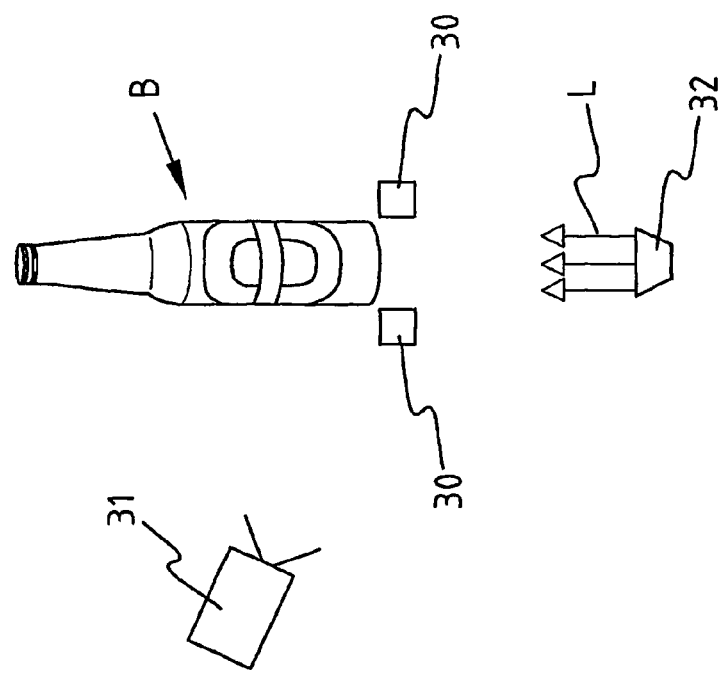

In FIGS. 9-12 several embodiments are shown for arranging camera and illumination positions with respect to each other and/or the bottle to be examined. In FIG. 9, a bottle B that is placed in the rotation head 30 is rotated as described in the above. The bottles is illuminated by means of the lamp or radiation means 32 through the bottom of the bottle.

Figure 11:
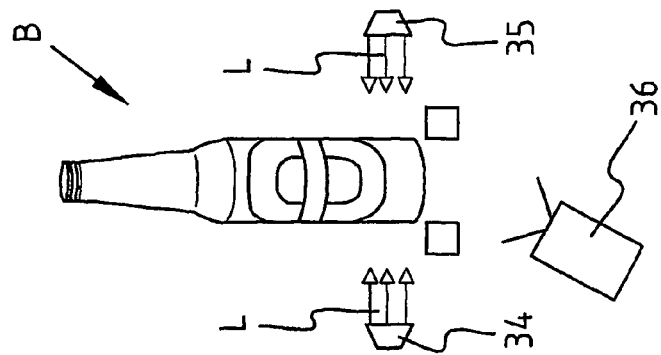
Figure 10:
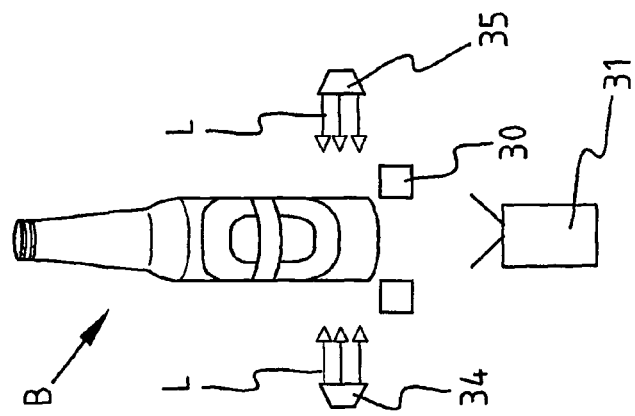

In FIG. 10 the bottle is illuminated from the sides by means of lights 34 and 35. The camera is positioned under the bottom of the bottle for taking images. In FIG. 11 the arrangement of FIG. 10 is altered in that the camera is placed at an angle with respect to the heart line of the bottle. Advantages of these embodiments are that the whole bottom area is recorded in a recording. A result hereof is that e.g. a glass particle can be spotted quicker and in several subsequent recordings. The inspection time can therefore be reduced. A further advantage is that when a process is used in which the bottle is dried before inspection, merely the bottom needs to be dried because the recordings are taken from below. Such drying of the bottom can be performed by means of quickly spinning the bottle, which spinning is advantageously performed for the detection process. Furthermore, an advantage of the skewed angle of the camera in FIG. 11 is that the recording is performed at an angle with respect to the rim of the head which means that detection in the utmost lower part of the bottom area in the bottle can more fully be performed. Also less dirt is likely to fall on the camera as it is positioned sideways with respect to the bottle.

A further advantageous embodiment (FIG. 12) comprises two lamps 34 radiating into the bottle from the sides and a prism 42 with three sides 39,40,41 for reflecting light. Also mirrors 44 are arranged in this embodiment for reflecting light. In this arrangement the light from the bottle can be detected by the camera from two sides, thereby improving the amount of information from the bottom area of the bottle that is recorded by the camera. In such an embodiment also 2 cameras can be deployed for capturing image data reflecting form the prism, or capturing the light directly from the mirrors. The possibility of e.g. a glass particle falling in the 'shadow' of the head 30 is thereby diminished.

Also as depicted in FIG. 13, a camera can be placed at an angle above the bottom area of the bottle, e.g. having vision through the shoulder of the bottle.

The taking of image recordings can e.g. be triggered by the orientation of the bottle or at a predetermined or a random time interval. The orientation of the bottle can in the first case e.g. be determined by means of a sensor.

The processing of the recorded images can be handled in several ways. Images with a substantially identical bottle orientation can be mutually subtracted and the difference image can be analysed with respect to residual information. Alternatively, the recorded image can be analysed with respect to an earlier recorded image by time shifting or back rotating towards the bottle orientation/position of the earlier recorded image and subsequently further processing thereof by means of e.g. the subtraction process. Also, a trajectory cam be determined and described of particles recorded on several images. Based on parameters of the trajectory the nature of the particle can be determined as being e.g. glass, which would lead to a bottle reject, or organic material, which would lead to an accepted bottle.

Different embodiments described in the foregoing can be freely combined. The rights sought are defined by the appended claims.

The invention claimed is:

1. Method for inspecting packagings for a liquid product, comprising:

setting a packaging into rotation relative to an image recording device, irradiating the packaging during the rotation with radiation of a predetermined wavelength, making at least one series of at least two two-dimensional image recordings of at least a part of the content of the packaging during the rotation with the image recording device, the image recording device being suitable for making two-dimensional recordings at the predetermined wavelength for detecting displacement of undesired particles, wherein during a two-dimensional image recording, the packaging is situated in a predetermined rotational position relative to the image recording device, and wherein the packaging is situated in substantially the same rotational position relative to the image recording device during successive two-dimensional image recordings of the series.

2. Method as claimed in claim 1, wherein successive two-dimensional image recordings of the series are made with an intervening time interval of a predetermined duration.

3. Method as claimed in claim 1, wherein the rotation speed is varied during the period in which the two-dimensional image recordings of a series are made.

4. Method as claimed in claim 1, wherein the rotation direction is varied during the period in which the two-dimensional image recordings of a series are made.

5. Method as claimed in claim 1, wherein a plurality of series of two-dimensional image recordings are made wherein two-dimensional image recordings of the same angle from different series are made successively.

6. Method as claimed in claim 1, comprising steps for comparing the image information from the two-dimensional images of a series to detect the presence of undesired particles in the packaging.

7. Method as claimed in claim 1, wherein the image recording device comprises a camera activated to make a two-dimensional image recording by a signal supplied from outside the camera by a rotation generating device.

8. Method as claimed in claim 1, wherein during performing of the method a packaging is placed in a holder comprising a drive unit, radiating means for generating the radiation, and position-determining means for determining the rotational position of the packaging.

9. The method as claimed in claim 1, wherein the radiation of the predetermined wavelength contacts the packaging at an angle greater than 90 degrees and less than 180 degrees from the packaging's axis of rotation.

10. The method as claimed in claim 1, wherein the packaging is maintained in rotation during the successive two-dimensional image recordings of the series.

11. The method as claimed in claim 1, wherein the undesired particles comprise glass particles.

12. System for inspecting a packaging for a liquid product, the system comprising:
a two-dimensional image recording device;
a rotator for rotating the packaging relative to the two-dimensional image recording device;
radiating means for irradiating the packaging during the rotation with radiation of a predetermined wavelength,
the two-dimensional image recording device, the image recording device being suitable for making two-dimensional image recordings at the predetermined wavelength for making at least one series of at least two two-dimensional image recordings of at least a part of the content of the packaging during the rotation for detecting displacement of undesired particles, wherein during a two-dimensional image recording, the packaging is situated in a predetermined rotational position relative to the image recording device,
orientation determining means for determining the rotational position of the packaging for making successive two-dimensional image recordings of the content of the packaging with the packaging being in substantially the same orientation relative to the two-dimensional image recording device.

13. The system as claimed in claim 12, wherein the undesired particles comprise glass particles.

14. A method for inspecting containers for a liquid product, comprising:
setting a container into rotation relative to an image recording device,
irradiating the container during the rotation with radiation of a predetermined wavelength,
making at least one series of at least two two-dimensional image recordings of at least a part of the content of the container during the rotation with the image recording device, the image recording device being suitable for making two-dimensional image recordings at the predetermined wavelength for detecting displacement of undesired particles, wherein during two-dimensional image recording, the packaging is situated in a predetermined rotational position relative to the image recording device, and wherein the container is situated in substantially the same rotational position relative to the image recording device during successive two-dimensional image recordings of the series;
wherein the image recording device is positionable at an angle ranging from greater than 90 degrees and less than 180 degrees from the container's axis of rotation.

15. The method as claimed in claim 14, wherein the radiation of the predetermined wavelength contacts the container at an angle greater than 90 degrees and less than 180 degrees from the axis of rotation.

16. The method as claimed in claim 14, and wherein the container is maintained in rotation during the successive two-dimensional recordings of the series.

17. The method as claimed in claim 14, wherein the undesired particles comprise glass particles.

* * * * *